United States Patent
Käseberg et al.

(10) Patent No.: US 12,023,109 B2
(45) Date of Patent: Jul. 2, 2024

(54) TECHNIQUE OF PROVIDING USER GUIDANCE FOR OBTAINING A REGISTRATION BETWEEN PATIENT IMAGE DATA AND A SURGICAL TRACKING SYSTEM

(71) Applicant: Stryker European Operations Limited, Carrigtwohill (IE)

(72) Inventors: Marc Käseberg, Biesenthal (DE); Markus Finke, Berlin (DE); Christian Winne, Berlin (DE)

(73) Assignee: Stryker European Operations Limited, Carrigtwohill (IE)

( * ) Notice: Subject to any disclaimer, the term of this patent is extended or adjusted under 35 U.S.C. 154(b) by 137 days.

(21) Appl. No.: 17/724,075

(22) Filed: Apr. 19, 2022

(65) Prior Publication Data

US 2022/0370147 A1 Nov. 24, 2022

(30) Foreign Application Priority Data

May 21, 2021 (EP) .................................... 21175196

(51) Int. Cl.
*G06T 7/73* (2017.01)
*A61B 34/10* (2016.01)
(Continued)

(52) U.S. Cl.
CPC .............. *A61B 34/20* (2016.02); *A61B 34/10* (2016.02); *A61B 90/37* (2016.02); *G06T 7/344* (2017.01);
(Continued)

(58) Field of Classification Search
None
See application file for complete search history.

(56) References Cited

U.S. PATENT DOCUMENTS 9,652,591 B2   5/2017   Moctezuma de la Barrera et al.
10,268,888 B2  4/2019   Osterhout et al.
(Continued)

FOREIGN PATENT DOCUMENTS

CN   106909771 A   6/2017
CN   108784832 A   11/2018
(Continued)

OTHER PUBLICATIONS

Kowalski, M. et al., "HoloFace: Augmenting Human-to-Human Interactions on Hololens," IEEE Winter Conference on Applications of Computer Vision (WACV), Lake Tahoe, NV, USA, 2018, pp. 141-149.

(Continued)

*Primary Examiner* — Robert J Craddock
(74) *Attorney, Agent, or Firm* — Howard & Howard Attorneys PLLC

(57) ABSTRACT

A method of providing user guidance. First patient image data of a patient's body is obtained. A registration instruction indicative of where to acquire a registration point relative to a surface of the body is determined. Second patient image data of the body, having been acquired by an augmented reality device, is obtained. A transformation between coordinate systems of the first and the second patient image data is determined. Based on the transformation, display of the registration instruction on a display of the AR device is triggered such that a user of the AR device is presented an augmented view with the registration instruction being overlaid onto the patient's body. The augmented view guides the user where to acquire the registration point. Also disclosed are a computing system, a surgical navigation system, and a computer program product.

20 Claims, 4 Drawing Sheets

(51) Int. Cl.
  *A61B 34/20* (2016.01)
  *A61B 90/00* (2016.01)
  *G06T 7/33* (2017.01)
  *G06T 19/00* (2011.01)

(52) U.S. Cl.
  CPC .................. *G06T 7/74* (2017.01); *G06T 7/75* (2017.01); *G06T 19/006* (2013.01); *A61B 2034/105* (2016.02); *A61B 2034/2065* (2016.02); *A61B 2090/365* (2016.02); *G06T 2207/30004* (2013.01); *G06T 2207/30201* (2013.01); *G06T 2210/41* (2013.01)

(56) References Cited

U.S. PATENT DOCUMENTS

| | | | |
|---|---|---|---|
| 10,366,489 | B2 | 7/2019 | Boettger et al. |
| 10,602,114 | B2 | 3/2020 | Casas |
| 10,846,851 | B2 | 11/2020 | Boettger et al. |
| 2017/0042631 | A1 | 2/2017 | Doo et al. |
| 2017/0186157 | A1 | 6/2017 | Boettger et al. |
| 2018/0185100 | A1 | 7/2018 | Weinstein et al. |
| 2019/0046276 | A1 | 2/2019 | Inglese et al. |
| 2019/0183576 | A1 | 6/2019 | Fahim et al. |
| 2019/0333213 | A1 | 10/2019 | Boettger et al. |

FOREIGN PATENT DOCUMENTS

| | | |
|---|---|---|
| CN | 109758230 A | 5/2019 |
| CN | 106909771 B | 7/2019 |
| CN | 110148453 A | 8/2019 |
| CN | 111465364 A | 7/2020 |
| DE | 102015226669 A1 | 6/2017 |
| EP | 3712900 A1 | 9/2020 |
| EP | 3975120 A1 | 3/2022 |
| WO | 2008008044 A2 | 1/2008 |
| WO | 2015164402 A1 | 10/2015 |
| WO | 2017144628 A1 | 8/2017 |
| WO | 2017144934 A1 | 8/2017 |
| WO | 2018232514 A1 | 12/2018 |
| WO | 2019118215 A1 | 6/2019 |

OTHER PUBLICATIONS

Abstract of NAVAB, Dr. Nassir, "Improving Depth Perception and Perception of Layout for In-Situ Visualization in Medical Augmented Reality", published online under http://campar.in.turn.de/Chair/ProjectDepthPerceptionMedicalAR.

English language abstract for CN 106909771 A extracted from espacenet.com database on Apr. 21, 2022, 2 pages.

English language abstract for CN 106909771 B extracted from espacenet.com database on Apr. 21, 2022, 2 pages.

English language abstract for CN 106909771 A extracted from espacenet.com database on Apr. 21, 2022, 10 pages.

English language abstract and machine-assisted English translation for CN 109 758 230 A extracted from espacenet.com database on Apr. 21, 2022, 14 pages.

English language abstract for CN 110148453 A extracted from espacenet.com database on Apr. 21, 2022, 2 pages.

English language abstract for CN 111465364 A extracted from espacenet.com database on Apr. 21, 2022, 2 pages.

English language abstract for DE 10 2015 226 669 A1 extracted from espacenet.com database on Apr. 21, 2022, 2 pages.

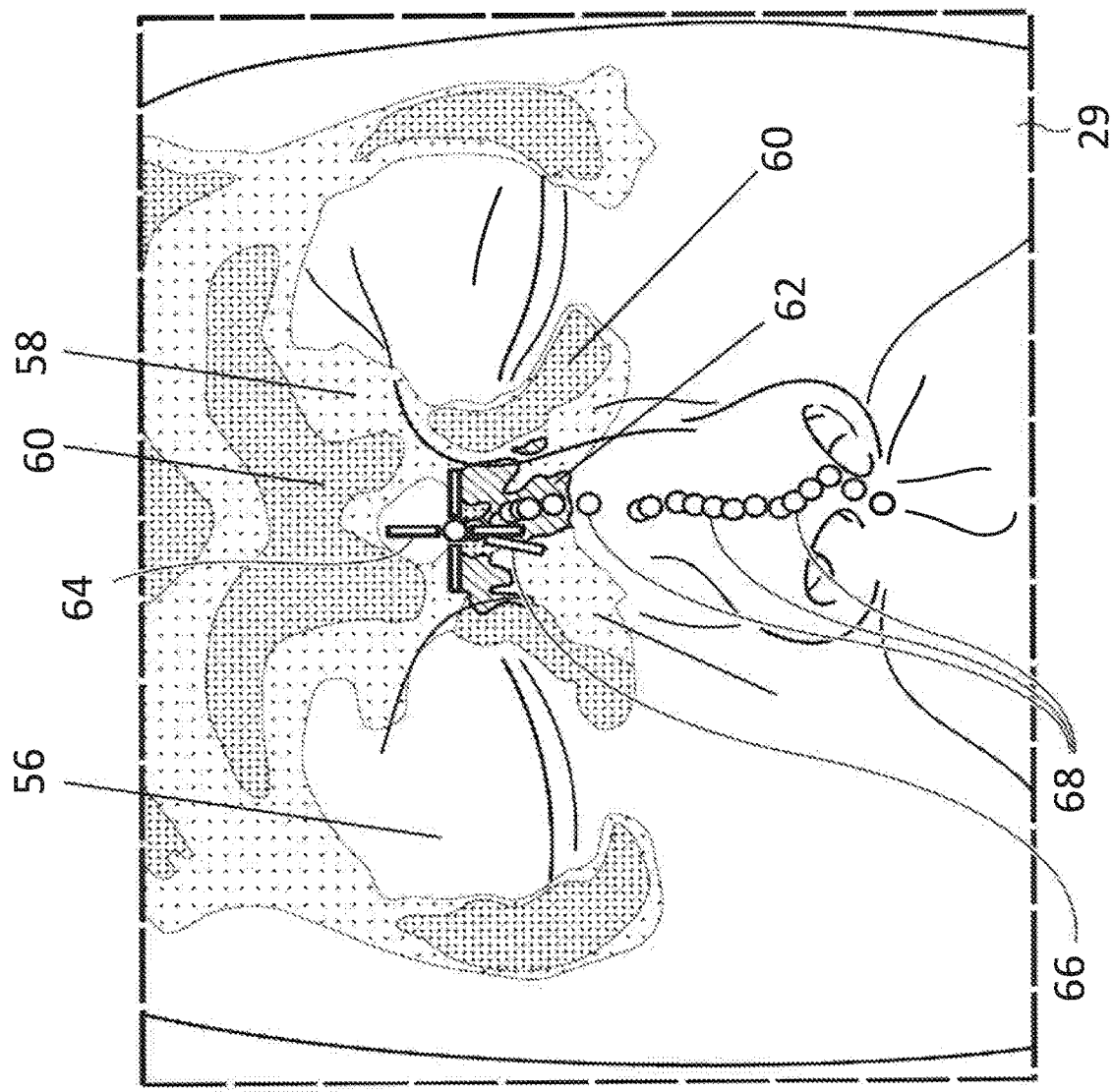

TECHNIQUE OF PROVIDING USER GUIDANCE FOR OBTAINING A REGISTRATION BETWEEN PATIENT IMAGE DATA AND A SURGICAL TRACKING SYSTEM

PRIORITY CLAIM

This application claims priority under 35 U.S.C. § 119 to European Patent Application No. 21175196.1, filed May 21, 2021, the entire contents of which are hereby incorporated by reference.

TECHNICAL FIELD

The present disclosure generally relates to a method of providing user guidance for obtaining a transformation between a coordinate system of patient image data and a coordinate system of a surgical tracking system. Also provided are a computing system, a surgical navigation system and a computer program product.

BACKGROUND

Surgical navigation has been used for some time to support medical staff. For example, a display of a current pose of a surgical instrument relative to patient image data may help a surgeon in moving the surgical tool to a desired anatomical location of the patient.

As is known in the art, a current pose of the surgical instrument may be tracked by an optical or electromagnetic surgical tracking system in a tracking coordinate system. For determining the current pose of the surgical instrument relative to the patient image data, a transformation between the tracking coordinate system and a coordinate system of the patient image data is required. This transformation is sometimes referred to as a registration between the surgical tracking system and the patient image data.

For obtaining the aforementioned registration, a surgeon or other medical staff may acquire one or more registration points on a surface of the patient's body using a registration probe tracked by the surgical tracking system. The so-acquired registration points may then be compared with the patient image data to obtain the registration.

Some areas of the body surface are more suitable for obtaining the registration points than others. It would therefore be advantageous to provide guidance for a surgeon or other medical staff where to acquire registration points on the surface of the patient's body in order to obtain an accurate registration between the surgical tracking system and the patient image data.

In certain scenarios, it may be advantageous to avoid a transformation between the tracking coordinate system and the coordinate system of the patient image data for providing the user guidance. In some scenarios, the guidance may be required before the surgical tracking system is activated or available.

SUMMARY

There is a need for a technique that solves one or more of the aforementioned or other problems.

According to a first aspect, a method of providing user guidance for obtaining a transformation between a coordinate system of patient image data and a coordinate system of a surgical tracking system is provided. The method comprises obtaining first patient image data of at least a portion of a patient's body, determining at least one registration instruction based on the first patient image data, the at least one registration instruction being indicative of where to acquire at least one registration point relative to a surface of the patient's body, obtaining second patient image data of at least the portion of the patient's body, the second patient image data having been acquired by an augmented reality (AR) device, determining a first transformation between a first coordinate system of the first patient image data and a second coordinate system of the second patient image data, and, based on the at least one registration instruction and the first transformation, triggering display of the at least one registration instruction on a display of the AR device such that a user of the AR device is presented an augmented view with the at least one registration instruction being overlaid onto at least the portion of the patient's body, the augmented view guiding the user where to acquire the at least one registration point.

The first patient image data may be (e.g., pre-operative or intra-operative) medical image data, for example having been acquired by a medical imaging device. The first patient image data may comprise computed tomography (CT) data, magnetic resonance (MR) data, ultrasonic image data or the like. The portion of the patient's body may comprise a surface of the body. The portion may comprise at least a part of a face of the patient.

One particular example for determining the first transformation will now be described. The first transformation may be determined based on the first patient image data and the second patient image data. The first transformation may be determined by matching the first patient image data to the second patient image data or vice versa. The first transformation may be determined by correlating the first patient image data with the second patient image data. The first transformation may be determined by matching a portion of the patient's body as represented by the first patient image data with a corresponding (e.g., the same) portion of the patient's body as represented by the second patient image data. The first transformation may be determined by comparing positions of similar landmarks in the first coordinate system and the second coordinate system with one another. This particular example for determining the first transformation may not require the AR device to be tracked by a tracking system.

The at least one registration instruction may comprise an indication of a subsection of a surface of the at least one portion of the patient's body, in which subsection the at least one registration point is to be acquired.

The subsection may be a part, an area or a segment of the surface of the at least one portion of the patient's body. The indication of the subsection may comprise a visualization of at least one of an outline and a content of the subsection.

The method may comprise receiving information indicative of the at least one acquired registration point, and processing the information indicative of the at least one acquired registration point for obtaining a second transformation between the first coordinate system of the first patient image data and a third coordinate system of a surgical tracking system.

The information indicative of the at least one acquired registration point may comprise an indication of a position of the at least one acquired registration point in the third coordinate system.

In one example, the information indicative of the at least one acquired registration point has been acquired by the surgical tracking system tracking a registration probe.

Processing the information indicative of the at least one acquired registration point may comprise matching a position of the at least one acquired registration point (e.g., in the third coordinate system) to the first patient image data (e.g., in the first coordinate system).

The position of the at least one acquired registration point may be matched to a body surface described by the first patient image data. The body surface may be described by or extracted from the first patient image data, for example as a three-dimensional point cloud, surface or shape. The position of the at least one registration point in the third coordinate system may be matched to the surface in the first coordinate system.

The method for example further comprises acquiring the information indicative of the at least one acquired registration point by obtaining at least one position of the registration probe in the third coordinate system, and determining the second transformation by matching the information indicative of the at least one acquired registration point to the first patient image data.

The method may further comprise obtaining tracking data describing a pose (e.g., at least one of position and orientation) of a surgical instrument in the third coordinate system, transforming the pose of the surgical instrument into the second coordinate system based on the first transformation and the second transformation, determining at least one navigation instruction associated with the pose of the surgical instrument in the second coordinate system, and triggering display of the at least one navigation instruction on the display of the AR device.

The at least one navigation instruction may comprise an indication of at least one of a type of the surgical instrument, a position of the surgical instrument in the second coordinate system and an orientation of the surgical instrument in the second coordinate system.

The portion of the patient's body may comprise one or more parts of a face of the patient, and determining the first transformation may comprise matching a generic face model to at least one of the first patient image data and the second patient image data. In this case, determining the first transformation may comprise determining a primary deformed face model by matching the generic face model to one of the first patient image data and the second patient image data, and comparing the primary deformed face model with the other of the first patient image data and the second patient image data to determine the first transformation. The generic face model may be matched to the one of the first patient image data and the second patient image data such that each of a plurality of predefined landmarks of the generic face model lies on a corresponding landmark of the portion of the patient's body in the one of the first patient image data and the second patient image data.

Comparing the primary deformed face model with the other of the first patient image data and the second patient image data may comprise comparing positions of landmarks identified by the deformed face model with positions of corresponding landmarks in the other of first patient image data and the second patient image data.

In one example, the corresponding landmark is a biometric feature of the patient's body.

The biometric feature may be at least one of a characteristic anatomical feature, a patient-specific feature and a feature of the surface of the patient's body.

The generic face model may be a three-dimensional morphable model (3D-MM). The generic face model may be matched to a (e.g., the) surface of the patient's body described by the at least one of the first patient image data and the second patient image data.

In a first variant, comparing the primary deformed face model with the other of the first patient image data and the second patient image data comprises determining a secondary deformed face model by matching the generic face model or the primary deformed face model to the other of the first patient image data and the second patient image data, and comparing (e.g., positions of predefined landmarks of) the primary deformed face model with (e.g., positions of corresponding predefined landmarks of) the secondary deformed face model.

In a second variant, comparing the primary deformed face model with the other of the first patient image data and the second patient image data comprises performing an image analysis on the other of the first patient image data and the second patient image data to determine a position of at least one of the corresponding landmarks in the other of the first patient image data and the second patient image data, and comparing the determined position of the at least one of the corresponding landmarks in the other of the first patient image data and the second patient image data with a position of one of the plurality of predefined landmarks of the primary deformed face model (e.g., the matched face model) that lies on the same corresponding landmark in the one of the first patient image data and the second patient image data.

The method may comprise determining whether a result of the comparing of (i) the primary deformed face model with (ii) the secondary deformed face model or the other of the first patient image data and the second patient image data fulfils one or more predefined acceptance criteria, and if the result fulfils the one or more predefined acceptance criteria, triggering display of the at least one registration instruction.

The one or mode predefined acceptance criteria may define at least one of a maximum (e.g., pointwise or average) spatial deviation, a maximum (e.g., pointwise or average) translational deviation, a maximum (e.g., pointwise or average) rotational deviation.

In one example, the method comprises instructing the surgical tracking system to start tracking after display of the at least one registration instruction has been triggered.

The method may comprise instructing the surgical tracking system to start tracking in response to display of the at least one registration instruction being triggered. The tracking system may not be active or available before the at least one registration instruction is triggered to be displayed.

The second patient image data may be indicative of (e.g., comprise, describe or consist of) a two-dimensional image acquired by a camera of the AR device. The second patient image data may have been acquired by a sensor of the AR device, for example a camera (e.g., a 2D camera, a time-of-flight (TOF) camera or a stereo camera) of the AR device. The second patient image data may comprise, describe of consist of at least one of two-dimensional image data, depth data, and three-dimensional image data.

According to a second aspect, a computing system is provided. The computing system comprises at least one memory and at least one processor, the at least one memory storing instructions which, when executed on the at least one processor, cause the at least one processor to carry out the method according to the first aspect.

According to a third aspect, a surgical navigation system is provided. The surgical navigation system comprises the computing system of the second aspect and at least one component chosen from the AR device, optionally configured as a head-mounted display (HMD) and the surgical tracking system. The surgical navigation system may be configured such that at least one object chosen from the AR device and the patient's body cannot be tracked by the surgical tracking system.

According to a fourth aspect, a computer program product is provided. The computer program product comprises program code portions for performing the method of the first aspect when the computer program product is executed on at least one processor, for example the at least one processor of the computing system according to the second aspect. The computer program product may be stored on one or more computer readable recording media, for example on the at least one memory of the computing system according to the second aspect.

BRIEF DESCRIPTION OF THE DRAWINGS

Further details, advantages and aspects of the present disclosure will become apparent from the following embodiments taken in conjunction with the drawings, wherein:

FIG. 4 shows a schematic example of an augmented view in accordance with the present disclosure.

DETAILED DESCRIPTION

Figure 1:
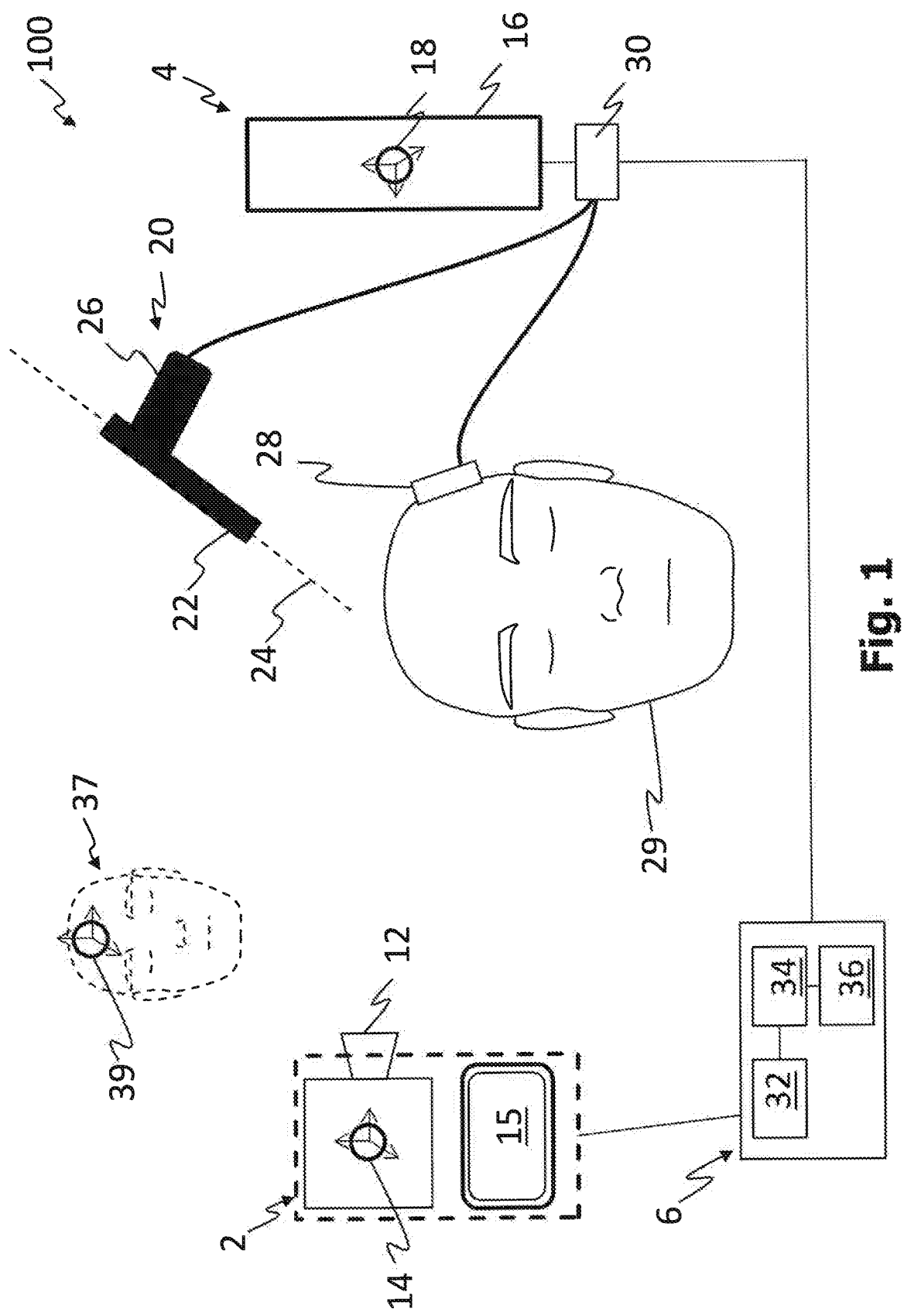
FIG. 1 shows an exemplary embodiment of a surgical navigation system in accordance with the present disclosure.

In the following description, exemplary embodiments of a method and a surgical navigation system will be explained with reference to the drawings. The same reference numerals will be used to denote the same or similar structural features.

FIG. 1 shows an exemplary embodiment of a surgical navigation system 100 in accordance with the present disclosure. The surgical navigation system 100 comprises an augmented reality (AR) device 2, a surgical tracking system 4 and a computing system 6.

The augmented reality device 2 comprises a camera 12 configured to acquire an image having a second coordinate system 14. The camera 12 may be configured to acquire a two-dimensional image, a depth image or a three-dimensional image.

The augmented reality device 2 further comprises a display 15. The display 15 may be a head-up display, for example comprising an at least partially transparent screen as a projection surface for visualizations to be displayed overlaid onto objects visible through the screen. Alternatively, the display 15 may comprise a display screen configured to display an image of a patient's body acquired by the camera 12, the image including visualizations overlaid onto the image of the patient's body. The display 15 may have a known, preferably fixed, pose (i.e., at least one of position and orientation) relative to the camera 12. This may enable displaying an object on the display 15, wherein the pose of the object is given in the second coordinate system. That is, triggering display of information (e.g., a pose of an instrument and/or information overlaid onto a patient's body) defined in or associated with the second coordinate system 14 may comprise transforming the information from the second coordinate system 14 into the coordinate system of the display 15 using a known pose of the display 15 in the second coordinate system 14. In one example, the second coordinate system 14 may correspond to the coordinate system of the display 15.

For example, the display 15 and the camera 12 are part of the same, for example portable, unit. The augmented reality device 2 may be configured as a head-mounted display (HMD), for example in the form of glasses. Examples of such HMDs include Microsoft's HoloLens and HoloLens 2.

The surgical tracking system 4 in the illustrated example is an electromagnetic tracking system comprising an electromagnetic field generator 16. The surgical tracking system 4 may alternatively be an optical tracking system using a camera or a stereo camera for tracking objects.

The surgical tracking system 4 is configured to track, in a third coordinate system 18, a surgical instrument 20. Examples of the surgical instrument 20 include a registration probe usable for acquiring a registration point, a pointer, a surgical drill guide, a surgical drill, a surgical chisel, a biopsy needle, a deep brain stimulation (DBS) electrode or the like. In the shown example, the surgical instrument 20 has an elongate tool shaft 22 defining a longitudinal tool axis 24, and a handle 26 to be gripped by a user. A tracker 28 is removably attached to a portion of a patient's body 29, for example using a biocompatible glue. The surgical tracking system 4 further comprises a localizer 30 configured to determine a current pose of the tracker 28 in the third coordinate system 18. The localizer 30 is further configured to determine a current pose of the surgical instrument 20 in the third coordinate system 18. The augmented reality device 2 in the shown example cannot be tracked by the surgical tracking system 4. This is because the augmented reality device is not equipped with an electromagnetic field sensor communicatively coupled to the localizer 30. In case an optical tracking system is used, the augmented reality device 2 may or may not comprise an optical tracking marker (tracker) trackable by the optical tracking system.

The computing system 6 comprises a memory 32, a processor 34 and a communication interface 36. The memory 32 stores instructions which, when executed on the processor 34, cause the processor 34 to carry out the method as disclosed herein. The augmented reality device 2 may be communicatively connected to the communication interface 36 of the computing system 6. Alternatively, the computing system 6 may be part of the AR device 2. The communication interface 36 is communicatively connected to the surgical navigation system 4, for example, its localizer 30. It is noted that the functionality of the localizer 30 may be implemented by the processor 34. That is, the localizer 30 may be part of the computing system 6. In one exemplary variant, the computing system 6 is part of the surgical tracking system 4.

Also indicated in FIG. 1 is first patient image data 37 having a first coordinate system 39. Details of how the first patient image data 37 may be used will be described in the following with reference to FIG. 2.

Figure 2:
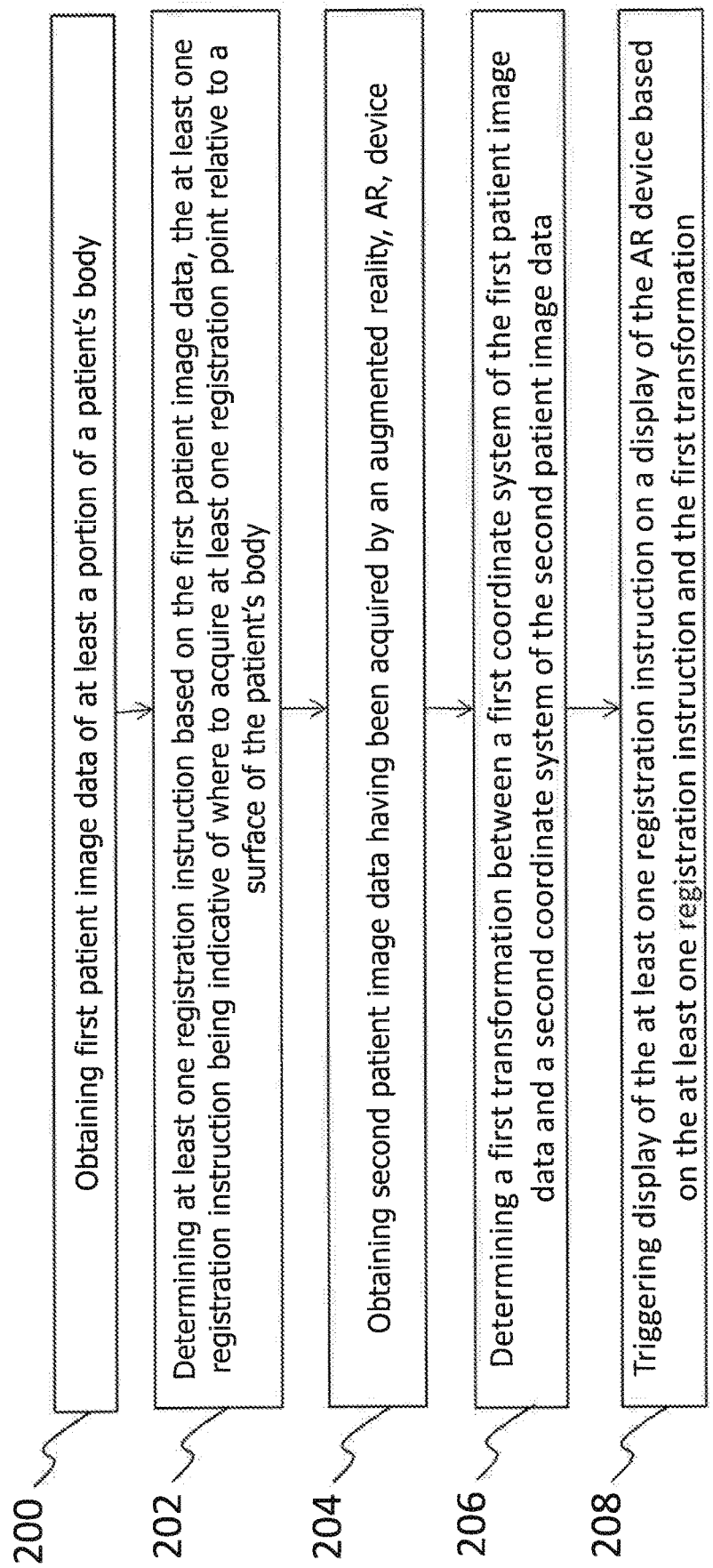
FIG. 2 shows an exemplary embodiment of a method in accordance with the present disclosure.

FIG. 2 shows an exemplary embodiment of a method in accordance with the present disclosure. The method may be performed by the processor 34 of the computing system 6. The method may be a computer-implemented data processing method. The method does not require any substantial physical interaction with the patient's body 29. In other words, the method does not include a surgical step.

In step 200, the first patient image data 37 of at least a portion of the patient's body 29 is obtained. The portion of the patient's body 29 may comprise a skin surface of the patient's body 29, for example a skin surface visible to a surgeon in a planned surgery. The portion of the patient's body 29 may comprise at least a part of a head of the patient, for example a face of the patient. The first patient image data 37 may comprise at least one of two-dimensional and three-dimensional medical image data. The first patient image data 37 may comprise one or more x-ray images of the portion of the patient's body 29. The first patient image data 37 may comprise a computed tomography (CT) image of the portion of the patient's body 29. The first patient image data 37 may comprise a magnetic resonance (MR) image of the portion of the patient's body. The first patient image data 37 may be preoperative image data. The first patient image data 37 may be obtained from the memory 32 or received via the interface 36, for example from a Picture Archiving and Communication System (PACS). It is noted that an acquisition of the first patient image data 37 by a medical imaging device may be performed beforehand, and may not be part of the method described herein. The obtained first patient image data 37 may have been acquired by the medical imaging device, wherein the medical imaging device may be connected to the PACS and/or the computing system 6.

In step 202, at least one registration instruction is determined based on the first patient image data 37. The at least one registration instruction may be determined only based on the first patient image data 37, for example automatically. The at least one registration instruction may be determined without requiring any user input. The at least one registration instruction is indicative of where to acquire at least one registration point relative to a surface of the patient's body 29. The at least one registration instruction may comprise an indication of a subsection of a surface of the at least one portion of the patient's body 29, in which subsection the at least one registration point is to be acquired.

The subsection may be determined by performing an image analysis of the first patient image data 37. The subsection may be determined by identifying a subsection of the surface of the patient's body described by the first patient image data 37 that has one or more predefined properties. The predefined properties may include at least one of the following: a low mechanical deformability, for example indicated by a distance between the surface and an underlying bone of the patient's body 29 falling under a predefined maximal distance; a surface curvature exceeding a minimum curvature; a surface curvature opposite to a surface curvature of a predefined surface area; a surface curvature deviating more than a predefined amount from a surface curvature of a predefined area (e.g., an area adjacent to or surrounding the subsection); a surface curvature opposite to or deviating more than a predefined amount from the remaining surface of the (e.g., portion of) the patient's body 29; a surface curvature deviating more than a predefined amount from a surface curvature at a position of at least one acquired registration point; a spatial distance to at least one acquired registration point exceeding a predefined amount. Other criteria for determining the at least one registration instruction are possible. For example, the at least one registration instruction may be determined by matching a predefined mask to the first patient image data 37, the matched predefined mask defining the subsection of the surface of the at least one portion of the patient's body 29. The at least one registration instruction may be determined as described in European patent application number 20198095.0 as filed 24 Sep. 2020, which is hereby incorporated in its entirety. Referring to claim 1 of this European patent application as filed, the image data may correspond to the first patient image data 37 described herein. Again referring to claim 1 of this European patent application as filed, the visualization of the priority value of the at least one surface point or the visualization of information derived from the priority value may correspond to the at least one registration instruction described herein.

In step 204, second patient image data of at least the portion of the patient's body 29 is obtained, the second patient image data having been acquired by the augmented reality (AR) device 2, for example the camera 12. The second patient image data may be indicative of (e.g., describe, comprise or consist of) two-dimensional or three-dimensional image data of at least the portion of the patient's body 29. The second patient image data may be obtained after or before step 200 and/or step 202. In one example, the camera 12 acquires video images and the AR device 2 or the computing system 6 determines, by performing an image analysis of the video images, whether a human face is depicted in one of the video images. The image for which a presence of the human face is detected in this manner may then be used as the second patient image data. The second patient image data may be received by the processor 34, for example via the communication interface 36.

In step 206, a first transformation is determined between the first coordinate system 39 of the first patient image data 37 and the second coordinate system 14 of the second patient image data. As mentioned above, the portion of the patient's body 29 may comprise one or more parts of a face of the patient. In this case, determining the first transformation may comprise matching a generic face model to at least one of the first patient image data 37 and the second patient image data. In an advantageous example, the generic face model is matched to the second patient image data that has been acquired by the camera 12 of the AR device 2. The generic face model may be a deformable face model, in particular a three-dimensional morphable face model. The generic face model may comprise a mesh, for example consisting of nodes connected by edges. Some or all of the nodes may designate or be associated with a predefined landmark.

Determining the first transformation may comprise determining a primary deformed face model by matching the generic face model to one of the first patient image data 37 and the second patient image data, and comparing the primary deformed face model with the other of the first patient image data 37 and the second patient image data to determine the first transformation. In the advantageous example, the generic face model is matched to the second patient image data to determine the primary deformed face model, which is then compared with the first patient image data 37.

The generic face model may be matched to the one of the first patient image data 37 and the second patient image data such that each of a plurality of predefined landmarks of the generic face model lies on a corresponding landmark of the portion of the patient's body 29 in the one of the first patient image data 37 and the second patient image data. In the advantageous example, the generic face model is matched to the second patient image data such that each of the plurality of predefined landmarks of the generic face model, for example each of the nodes, lies on a corresponding landmark of the portion of the patient's body 29 in the second patient image data that has been acquired by the camera 12.

Matching the generic face model to the one of the first patient image data 37 and the second patient image data may comprise matching the generic face model to a surface of the portion of the patient's body as described by the one of the first patient image data 37 and the second patient image data. The surface may be defined by a three-dimensional point cloud comprising three-dimensional coordinates of points of the point cloud, or by an algebraic or numerical definition of a three-dimensional surface. Matching the generic face model to the one of the first patient image data 37 and the second patient image data may comprise extracting the surface from the one of the first patient image data 37 and the second patient image data. For example, the three-dimensional point cloud comprises at least one point for each of the corresponding landmarks. In one example, the generic face model is matched to one or more two-dimensional images comprised in the second patient image data, for example to a first two-dimensional image acquired by a first image acquisition unit and a second two-dimensional image acquired by a second image acquisition unit, wherein the first and the second image acquisition unit are comprised in the camera 12. A comparison of each face model matched to a two-dimensional image may be performed to determine the primary deformed face model.

The generic face model may define deformational properties that limit a deformation of at least parts of the generic face model, for example relative to other parts of the generic face model. The deformational properties may ensure that the deformed face model still represents a realistic form of a human face (e.g., even if the generic face model is matched to a two-dimensional image). Matching the generic face model to the one of the first patient image data 37 and the second patient image data may comprise aligning the generic face model with (e.g., the surface of the portion of the patient's body as described by) the one of the first patient image data 37 and the second patient image data. The alignment may comprise using an alignment optimization algorithm. After the alignment, the aligned generic face model may be deformed to minimize deviations between the aligned generic face model and the one of the first patient image data 37 and the second patient image. For the alignment and the deformation of the generic face model, positions of predefined landmarks of the generic face model may be adjusted to correspond to positions of corresponding landmarks on the surface of the patient's body as described by or depicted in the one of the first patient image data 37 and the second patient image. The corresponding landmark may be at least one of an anatomical landmark of the patient's body 29, a characteristic surface feature of the patient's body 29, and a biometric feature of the patient's body 29. The biometric feature may be a patient-specific feature. Therefore, relative positions between biometric features may differ from one patient to another.

Figure 3:
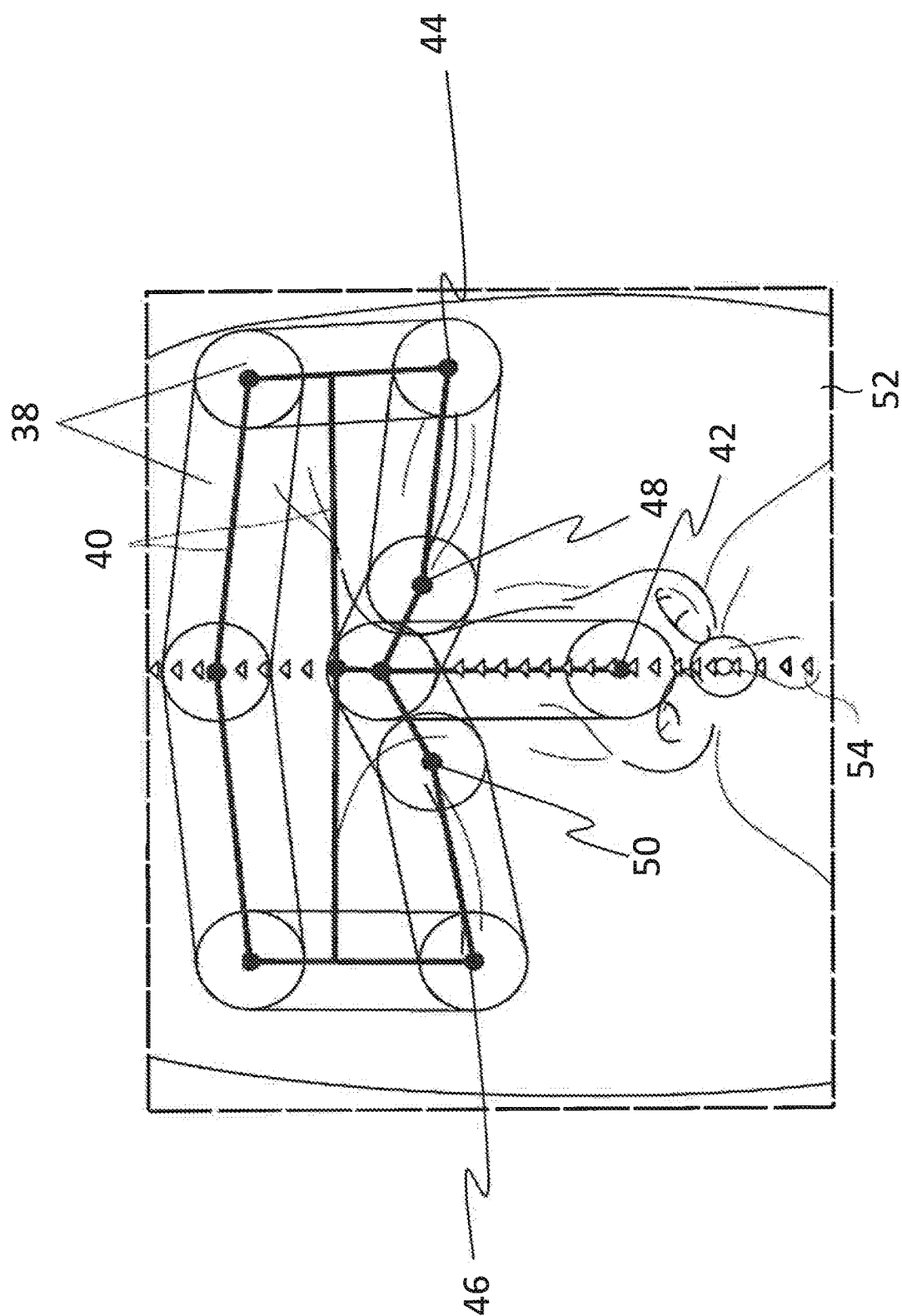
FIG. 3 shows a schematic illustration of a primary deformed face model in accordance with the present disclosure.

FIG. 3 shows a schematic illustration of a primary deformed face model 38 in accordance with the present disclosure. In this example, the generic face model and the primary deformed face model 38 each consist of ten nodes and eleven edges 40. A first node 42 is associated with a node tip, a second node 44 is associated with an outer left eye corner, a third node 46 is associated with an outer right eye corner, a fourth node 48 is associated with an inner left eye corner and a fifth node 50 is associated with an inner right eye corner. Each of the nodes 42-50 corresponds to a predefined landmark of the face model and is matched to a corresponding biometric feature of the second patient image data 52. That is, the biometric feature may be an outer eye corner, an inner eye corner, a nose tip or the like. Also shown in FIG. 3 is a predefined symmetry plane 54 of the matched face model 38 that may additionally be matched to the second patient image data 52 for determining or improving the primary deformed face model 38. It is apparent that FIG. 3 serves an illustrative purpose and other shapes and types of the generic face model or the primary deformed face model may be used.

Continuing the explanation of step 206, in a first variant, comparing the primary deformed face model with the other of the first patient image data 37 and the second patient image data 52 comprises determining a secondary deformed face model. The secondary deformed face model is obtained by matching the generic face model or the primary deformed face model 38 to the other of the first patient image data 37 and the second patient image data 52 and comparing the primary deformed face model 38 with the secondary deformed face model. Matching the generic face model or the primary deformed face model 38 to the other of the first patient image data 37 and the second patient image data 52 may involve, similarly to the first matching operation described above, extracting a surface from the other of the first patient image data 37 and the second patient image data 52, and aligning and deforming the generic face model or the primary deformed face model 38 to represent a shape of at least a part of the three-dimensional surface. It is noted that the schematic illustration shown in FIG. 3 and the description thereof may similarly apply to the secondary deformed face model as described herein.

In a second variant, comparing the primary deformed face model 38 with the other of the first patient image data 37 and the second patient image data 52 comprises performing an image analysis on the other of the first patient image data 37 and the second patient image data 52 to determine a position of at least one of the corresponding landmarks of the portion of the patient's body 29 in the other of the first patient image data 37 and the second patient image data 52. In this case, the method may further comprise comparing the determined position of the at least one of the corresponding landmarks in the other of the first patient image data 37 and the second patient image data 52 with a position of one of the plurality of predefined landmarks of the matched generic face model or the primary deformed face model 38 that lies on the same corresponding landmark in the one of the first patient image data 37 and the second patient image data.

In the advantageous example, the image analysis is performed on the first patient image data 37, which may comprise preoperative CT image data of the patient's body 29, to determine the position of the at least one of the corresponding landmarks in the first patient image data 37. This may involve extracting a body surface from the first patient image data 37 and analyzing the shape of the extracted body surface to identify the position of the corresponding landmarks, for example a position of a nose tip, an outer right eye corner, an inner left eye corner and so on. The positions identified in the first patient image data 37 may then be compared with the positions of the predefined landmarks of the deformed face model 38 that are matched to the same landmark in the second patient image data 52. The position of the outer right eye corner may be identified in the first patient image data 37 and compared with the position of the node 46 of the primary deformed face model 38 that was obtained by matching the generic face model to the second patient image data 52. The position of the inner left eye corner may be identified in the first patient image data 37 and compared with the position of the node 48 of the primary deformed face model 38. Such a comparison may be performed for some of or all of the predefined landmarks or nodes. Put differently, a plurality of positions of landmarks in the first patient image data 37 may be compared with a plurality of positions of similar landmarks in the second patient image data 52 as defined by the primary deformed face model 38. In other words, the positions of similar landmarks in the first coordinate system 39 and the second coordinate system 14 may be compared with one another.

The comparison of the position(s) may be used for determining the first transformation. The position of a landmark in the first patient image data 37 is given in the first coordinate system 39, whereas a position of a predefined landmark of the generic face mask after being matched to the corresponding landmark in the second patient image data 52 is given in the second coordinate system 14. Comparing these two positions with one another may yield a transformation between the first coordinate system 39 and the second coordinate system 14. Generally speaking, the more positions in the two coordinate systems 39, 14 are compared with one another, the more accurate is the obtained first transformation. For example, at least three positions are compared to obtain the first transformation, which may comprise a translational and a rotational component. A point-to-point matching algorithm may be employed for comparing the positions, wherein a result of the point-to-point matching may be the first transformation. An optimization algorithm may be used for determining a best match between the positions to determine the first transformation. The optimization algorithm may be or incorporate an iterative closest point (ICP) algorithm.

Again referring to FIG. 2, in step 208, based on the at least one registration instruction and the first transformation, display of the at least one registration instruction is triggered on the display 15 of the AR device 2 such that a user of the AR device 2 is presented an augmented view with the at least one registration instruction overlaid onto at least the portion of the patient's body 29. The augmented view guides the user where on the surface of the patient's body 29 to acquire the at least one registration point.

As noted above, a spatial relationship between the camera 12 and the display 15 may be fixed and/or known. Put differently, a transformation between the second coordinate system and a coordinate system of the display 15 may be known. This enables displaying objects on the display 15 using their pose as described in the second coordinate system. It is evident that this approach is applicable to any object, text or instruction to be displayed. An object's or an instruction's pose may be transformed from the second coordinate system 14 into the coordinate system of the display 15 by the augmented reality device 2 and/or the processor 34. For example, step 208 may comprise determining a pose (i.e., at least one of a position and an orientation) of the registration instruction in the coordinate system of the display 15 by transforming (e.g., a pose of) the registration instruction (e.g., as described in the second coordinate system) into the coordinate system of the display 15 using the known transformation between the second coordinate system and the coordinate system of the display 15.

FIG. 4 shows a schematic example of an augmented view in accordance with the present disclosure. In case the display 15 comprises an at least partially transparent screen through which the portion of the patient's body 29 can be seen by a user of the AR device 2, only the at least one registration instruction may be displayed on the screen. In this case, or if the display 15 is a head-up display or another type of semitransparent or holographic display, the portion of the patient's body 29 may be visible through the display 15 of the augmented reality device 2. Alternatively, if the display 15 comprises a display screen through which the portion of the patient's body 29 cannot be seen by the user of the AR device 2, the at least one registration instruction may be displayed on the screen overlaid onto an image of the patient's body 29 acquired by the camera 12, for example an image comprised in the second patient image data 52. A live video of the patient's body 29 acquired by the camera 12 may be displayed on the display 15 to provide the user of the AR device 2 with the augmented view.

The augmented view may comprise the at least one registration instruction overlaid onto at least the portion of the patient's body 29, even if a relative position between the camera 12 and the patient's body 29 has changed between the time of acquiring the second patient image data and the time of displaying the augmented view. The AR device 2 or the computing system 6 may (e.g., continuously or periodically) update the displayed augmented view depending on a current pose of the AR device 2 relative to the patient's body 29. For example, steps 204-208 are performed periodically. That is, second patient image data 52 may be obtained once more, the first transformation may be determined in step 206 based on the most recently acquired second patient image data 52, and the transformation used in step 208 may be the most recently determined first transformation. Alternatively or additionally, the method may comprise determining a first pose of the AR device 2 (e.g., the camera 12) in a world coordinate system at the time the second patient image data has been acquired by the AR device 2. The method may further comprise determining a pose of the patient's body 29 in the world coordinate system, for example by locating the portion of the patient's body 29 in the world coordinate system. This may involve identifying the positions of the landmarks in the second patient image data 52 and transforming the positions from the second coordinate system 14 to the world coordinate system using the first pose of the AR device 2, if these two coordinate systems are not equal. The method may further comprise determining a second pose of the AR device 2 in the world coordinate system at the time the display of the at least one registration instruction is triggered once again (i.e., at a time after step 208 has been performed for the first time). The augmented view may then be determined based on the at least one registration instruction, the first transformation and a result of a comparison of the first pose with the second pose. That is, a translational and/or rotational shift of the AR device 2 relative to the patient's body 29 after the time point(s) of acquiring the second patient image data 52 may be compensated, such that the augmented view always provides the user of the AR device 2 with the at least one registration instruction overlaid onto the portion of the patient's body 29. In this case, the first registration does not necessarily need to be updated, only the second pose of the AR device 2 in the word coordinate system. The pose of the AR device 2 in the world coordinate system may be determined using data from one or more sensors comprised in the AR device 2, for example (e.g., the second patient) image data from the camera 12, data from a depth sensor, a time-of-flight camera, an accelerometer, a gyroscope or the like.

In the shown example, the patient's body 29 has a first surface subsection 56 on top of which no registration instruction is displayed. The at least one registration instruction comprises an indication of subsections 58 and 60. Each of the subsections 58, 60 of the patient's surface may be highlighted in a different manner. For example, the indications of the subsections 58 and 60 may differ from one another in at least one of color, opacity or optical pattern.

The subsection 56 on the right eyelid of the patient's body 29 is not highlighted. This may be because it is disadvantageous to acquire the at least one registration point on the right eyelid, as this body portion is highly deformable. For instance, when acquiring a registration point on such highly deformable body portions, the position of the acquired registration point significantly depends on the pressure with which the registration probe is pressed onto the body surface. The subsections 58 are more favorable for acquiring the at least one registration point, as they designate areas having a lower mechanical deformability, indicated by a lower distance between the body surface and a bone of the patient's body underneath the body surface. The subsections 60 are the most preferred regions for acquiring the at least one registration point, as they have a higher surface curvature than the subsections 60. For details on how the subsections 56, 58 and 60 may be determined, it is referred to the description of step 202 above.

The at least one registration instruction may be conditionally triggered to be displayed. For example, the method may comprise determining whether a result of the comparing of (i) the primary deformed face model 38 with (ii) the secondary deformed face model or the other of the first patient image data 37 and the second patient image data 52 fulfils one or more predefined acceptance criteria. The method may comprise, (e.g., only) if the result fulfils the one or more predefined acceptance criteria, triggering display of the at least one registration instruction. For example, the one or more predefined acceptance criteria comprise a maximum deviation of a position of one or more of the predefined landmarks or a maximum average deviation of positions of a set or all of the predefined landmarks. The deviation may be a translational deviation in one or more predefined spatial directions, a rotational deviation around one or more predefined axes or a combination thereof. This approach may ensure that the at least one registration instruction is only displayed if the accuracy of the first transformation is acceptable, thereby avoiding a misaligned display of the at least one registration instruction.

For example, a degree of similarity is determined between (i) the primary deformed face model 38 and (ii) the secondary deformed face model or the other of the first patient image data 37 and the second patient image data 52, and it is determined whether the degree of similarity fulfils the one or more predefined acceptance criteria. The method may comprise, (e.g., only) if the degree of similarity fulfils the one or more predefined acceptance criteria, triggering display of the at least one registration instruction. The degree of similarity may be a difference or quotient between at least one geometrical property of the primary deformed face model 38 and the secondary deformed face model or (e.g., the surface described by or extracted from) the other of the first patient image data 37 and the second patient image data 52. For example, the one or more predefined acceptance criteria may define that the distance between the matched node 46 and the matched node 44, divided by the distance between the matched node 50 and the matched node 48, must be similar between the primary deformed face model 38 and the secondary deformed face model to within a predefined degree of tolerance, such as 5%, 10% or 12%. The predefined acceptance criteria may define that the primary deformed face model 38 must be matched to a same patient as the secondary deformed face model. The display of the at least one registration instruction may only be triggered in case the same patient is depicted in the first patient image data 37 and the second patient image data 52. A biometric identification algorithm may be used to correctly identify a patient based on the first patient image data 37 and the second patient image data 52 respectively, for example using at least one of the primary deformed face model 38 and the secondary deformed face model.

At the time of triggering display of the at least one registration instruction, the patient's body 29 may not be tracked by the surgical tracking system 4. For example, before display of the at least one registration instruction has been triggered, the patient's body 29 cannot be tracked by the surgical tracking system 4 or the surgical tracking system 4 may be deactivated. The method disclosed herein may comprise instructing the surgical tracking system 4 to start tracking after display of the at least one registration instruction has been triggered, for example in response to display of the at least one registration instruction being triggered.

The method may further comprise obtaining or determining a second transformation between the first coordinate system 39 of the first patient image data 37 and the third coordinate system 18 of the surgical tracking system 4. One may say that a chain of the first and second transformations connect the second coordinate system 14 of the AR device 2 with the third coordinate system 18 of the surgical tracking system 4 via the first coordinate system 39 of the first patient image data 37. For example, the method comprises receiving information indicative of the at least one acquired registration point, and processing the information indicative of the at least one acquired registration point for obtaining the second transformation. The information indicative of the at least one acquired registration point may have been acquired by the surgical tracking system 4 tracking a registration probe, for example the surgical instrument 20. In other words, the information indicative of the at least one acquired registration point may have been acquired using the registration probe tracked by the surgical tracking system 4. The information may be received from the surgical tracking system 4, for example the localizer 30, via the communication interface 36. Once the information indicative of the at least one acquired registration point has been received or the second transformation has been determined, the method may once again determine the at least one registration instruction, this time based on the first patient image data 37 and at least one of the information indicative of the at least one acquired registration point and the second transformation. The displayed at least one registration instruction may be updated based on at least one of the information indicative of the at least one acquired registration point and the second transformation.

For instance, a user may place a distal end of the registration probe onto a contact point on the surface of the patient's body 29. The information indicative of the at least one acquired registration point may comprise the position of this contact point in the third coordinate system 18. The information indicative of the at least one acquired registration point may comprise a position of the at least one acquired registration point in the third coordinate system 18 of the surgical tracking system 4. Alternatively or additionally, the information indicative of the at least one acquired registration point may comprise the pose of the registration probe in contact with the surface of the patient's body 29. Based on a known spatial relationship between the registration probe and the surface of the patient's body, for example based on a predefined distance between a tracker attached to the registration probe and the distal end of the registration probe, the position of the contact point of the registration probe with the surface of the patient's body 29 may be determined, for example by the computing system 6. This contact point may correspond to or be used as the at least one acquired registration point. The user may instruct the surgical navigation system 100, in particular the localizer 30 or the computing system 6, when to acquire a registration point, for example by pressing a foot pedal of the surgical navigation system 100, pressing a button on the registration probe to send a command to the surgical navigation system 100, speaking a control command recognizable by an audio interface of the surgical navigation system 100, or the like.

Processing the information indicative of the at least one acquired registration point may comprise matching a position of the at least one acquired registration point to the first patient image data 37. The method may comprise acquiring the information indicative of the at least one acquired registration point by obtaining at least one position of the registration probe in the third coordinate system 18, and determining the second transformation by matching the information indicative of the at least one acquired registration point to the first patient image data 37.

The position of the acquired at least one registration point in the third coordinate system 18 may be matched, for example using a point-to-surface matching algorithm, to the surface of the patient's body 29 described by, detected in or extracted from the first patient image data 37. For example, the first patient image data 37 is a three-dimensional CT image of a head of the patient. An image analysis algorithm may be used to detect the body surface within the CT image, for example using a minimum and a maximum Hounsfield value of CT image voxels, conducting outlier removal and surface smoothing. The detected body surface may correspond to the extracted three-dimensional point cloud or surface described above. Other techniques for detecting a body surface in patient image data may also be used. The matching of the position(s) of the at least one registration point in the third coordinate system 18 to the surface of the patient's body 29 extracted from the first patient image data 37 may comprise matching the position(s) of the at least one registration point in the third coordinate system 18 to the three-dimensional point cloud in the first coordinate system 39. This approach may be referred to as point-to-point matching. Alternatively, the matching of the position(s) of the at least one registration point in the third coordinate system 18 to the surface of the patient's body 29 detected in the first patient image data 37 may comprise matching the position(s) of the at least one registration point in the third coordinate system 18 to the three-dimensional surface in the first coordinate system 39. This approach may be referred to as point-to-surface matching.

The method may further comprise obtaining tracking data describing a pose of the surgical instrument 20 in the third coordinate system 18, and transforming the pose of the surgical instrument 20 into the second coordinate system 14 based on the first transformation and the second transformation. Referring to FIG. 1, it is apparent that a pose in the third coordinate system 18 can be transformed into a pose in the second coordinate system 14 using the first and the second transformation. That is, the pose may be transformed from the third coordinate system 18 into the first coordinate system 10 using the second transformation that has been obtained as described above. The pose may then be transformed from the first coordinate system 10 to the second coordinate system 14 using the first transformation that has been obtained as described above. Of course, the method may comprise determining a combined transformation based on the first and the second transformation to transform the pose directly from the third coordinate system 18 into the second coordinate system 14. The pose of the surgical instrument 20 may be transformed from the third coordinate system 18 into the world coordinate system using the second transformation, the first transformation and a transformation between the second coordinate system 14 and the world coordinate system determined based on the first pose of the AR device 2 in the world coordinate system. The pose of the surgical instrument 20 may be transformed from the world coordinate system into the second coordinate system 14 based on a (e.g., comparison of the first pose of the AR device 2 with a) current pose of the AR device 2 determined in the world coordinate system. As noted above, the pose of the surgical instrument 20 in the second coordinate system 14 may be transformed into the coordinate system of the display 15 using the known transformation between the second coordinate system and the coordinate system of the display 15.

The method may comprise determining at least one navigation instruction associated with the pose of the surgical instrument 20 in the second coordinate system 14 (or, e.g., in the third coordinate system or in the world coordinate system). The at least one navigation instruction may include at least one of an indication of a type, an indication of a position and an indication of an orientation of the surgical instrument 20 in the second coordinate system 14 (or, e.g., in the third coordinate system or in the world coordinate system). The method may further comprise triggering display of the at least one navigation instruction on the display 15 of the AR device 2, advantageously in an augmented view overlaid onto the patient's body 29. The (e.g., indication of the) position and the (e.g., indication of the) orientation of the surgical instrument 20 in the third coordinate system may be transformed into the world coordinate system or into the second coordinate system 14 based on the first transformation and the second transformation. The (e.g., indication of the) position and the (e.g., indication of the) orientation of the surgical instrument 20 in the world coordinate system may be transformed into the second coordinate system 14 using a third pose of the augmented reality device 2 at a time of triggering display of the at least one navigation instruction, in particular a pose of the camera 12, determined in the world coordinate system. That is, as explained above for the at least one registration instruction, the method may comprise determining a third pose of the AR device 2 in the world coordinate system at the time the display of the at least one navigation instruction is triggered to be displayed. The first pose of the AR device 2 in the world coordinate system at the time of acquiring the second patient image data may be compared with the third pose to compensate a translational and/or rotational shift of the AR device 2 relative to the patient's body 29 after the time point(s) of acquiring the second patient image data 52. The display 15 may provide the user of the AR device 2 with the at least one navigation instruction (e.g., overlaid onto the portion of the patient's body 29), irrespective of a change in relative orientation between the AR device 2 and the patient's body 29 over time.

Referring again to FIG. 4, the augmented view comprises the at least one navigation instruction. In particular, the augmented view comprises a pair of crosshairs 64 indicating a position of a tip of the registration probe tracked by the surgical tracking system 4. The augmented view further comprises a line 66 indicating an orientation of a main axis of the registration probe, for example the axis 24. It is noted that for this at least one navigation instruction to be displayed, the second transformation may be required. Therefore, the at least one navigation instruction shown in FIG. 4 may only be displayed once the second transformation has been obtained or determined as disclosed herein.

Further visualized in FIG. 4 are positions of a plurality of registration points 68 that have already been acquired using the registration probe. These positions are visualized overlaid onto the contact points on the surface of the patient's body 29 where the registration points 68 have been acquired with the tracked registration probe. This informs the user where on the surface of the patient's body 29 registration points have already been acquired. In the shown illustration, a user has moved the registration probe on the surface of the patient's body 29 starting at the philtrum and proceeding in direction of the glabella. Parts 62 of the areas 58, 60 that are covered with the acquired registration points 68 are highlighted in a different manner than the areas 58, 60 to inform the user where no additional registration points are to be acquired.

For example, the parts 62 may correspond to parts of the areas 58, 60 that are within a predefined distance from one or more of the acquired registration points 68 and/or that have a surface curvature deviating from a (e.g., average) surface curvature at the (e.g., one or more) acquired registration point(s) 68 less than a predefined threshold. Further criteria for determining the parts 62 may be applied. In this respect, it is also referred to European patent application number 20198095.0 as filed 24 Sep. 2020, in particular the determination of the fourth and fifth weighting factor described therein.

As noted above, the method may proceed by updating the display of the at least one registration instruction, for example by determining a new at least one registration instruction not only based on the first patient image data 37, but also based on the acquired at least one registration point and the second registration, and triggering display of the new at least on registration instruction as in the case of the at least one registration instruction. In other words, the augmented view shown in FIG. 4 may be (e.g., periodically or continuously) updated depending on the number and positions of the acquired registration points. The updating of the augmented view may comprise adding newly acquired registration points and changing the areas 56, 58, 60, 62 accordingly. The second transformation may be updated from time to time, for example every time a predefined number of new registration points has been acquired or upon reception of a user command. This may iteratively improve the accuracy of the second transformation, and thereby also improve the accuracy of the at least one navigation instruction displayed overlaid onto the patient's body 29. The second transformation and the display of the at least one registration instruction may be continuously updated during the acquisition of registration points as described in European patent application number 20198095.0 as filed 24 Sep. 2020 with reference to the fourth and fifth weighting factor.

It is once again noted that the present disclosure also covers variants in which the first pose of the AR device 2 is determined in the world coordinate system, and a transformation between the second coordinate system 14 and the world coordinate system is determined using the first pose and the first transformation. The at least one registration instruction and/or the at least one navigation instruction may be determined with reference to the world coordinate system. To display the at least one registration instruction or the at least one navigation instruction on the display 15, a transformation between the world coordinate system and the second coordinate system 14 or the coordinate system of the display 15 may be determined, for example based on the current, second or third pose of the AR device 2 in the world coordinate system or a comparison thereof with the first pose of the AR device 2 in the world coordinate system. This may enable displaying the at least one registration instruction and/or the at least one navigation instruction in a fixed spatial relationship relative to the patient's body 29, even if the relative position between the AR device 2 and the patient's body 29 changes after the first transformation has been determined.

Also provided are a computer program product comprising program code portions for performing the method as disclosed herein, when the computer program product is executed on at least one processor such as the processor 34. The computer program product may be stored on one or more computer readable, for example non-transitory, recording media such as the memory 32. A computer program comprising program code portions for performing the method as disclosed herein, when the computer program is executed on at least one processor such as the processor 34, may also be provided. The computer program may be stored on a recording medium such as the memory 32 or transmitted as a digital or analog data carrier signal or signal wave. Numerous modifications of the embodiments described herein may be possible. For example, the sequence of the method steps described herein may be changed. Not all method steps may be required or essential.

The present disclosure may provide for an advantageous method of providing user guidance for obtaining a registration between the first patient image data 37 and the surgical tracking system 4. A user of the AR device 2 may be presented with an augmented view comprising at least one registration instruction overlaid onto the patient's body 29. The registration instruction may guide the user where on the surface of the patient's body 29 to acquire a registration point with a registration probe tracked by the surgical tracking system 4. This may help the user in acquiring the registration points, for example in a repeatable manner.

At least the steps 200-208 of the method disclosed herein may not require the surgical tracking system 4 to be present or active. This may be advantageous in case a user wants to check the registration instructions before transferring the patient to an operating room in which the surgical tracking system 4 is located or before the surgical tracking system 4 has been set up.

The surgical tracking system 4 may not be required to track the AR device 2. This may be advantageous in case the surgical tracking system 4 is not capable of tracking the AR device 2, for example if the AR device 2 does not comprise a tracker locatable by the surgical tracking system 4 in the third coordinate system 18.

The method may use a face model for obtaining a transformation between the first coordinate system 39 and the second coordinate system 14. This may improve the accuracy of the obtained first transformation and may reduce processing effort. Furthermore, commonly available AR devices may be structurally optimized for image analysis using face models, which means the method described herein may be implemented without requiring sophisticated hardware.

The invention claimed is:

1. A method of providing user guidance for obtaining a transformation between a coordinate system of patient image data and a coordinate system of a surgical tracking system, the method comprising:
    obtaining first patient image data of at least a portion of a patient's body;
    determining at least one registration instruction based on the first patient image data, the at least one registration instruction being indicative of where to acquire at least one registration point relative to a surface of the patient's body;

obtaining second patient image data of at least the portion of the patient's body, the second patient image data having been acquired by an augmented reality, AR, device;

determining a first transformation between a first coordinate system of the first patient image data and a second coordinate system of the second patient image data; and based on the at least one registration instruction and the first transformation, triggering display of the at least one registration instruction on a display of the AR device such that a user of the AR device is presented an augmented view with the at least one registration instruction being overlaid onto at least the portion of the patient's body, the augmented view guiding the user where to acquire the at least one registration point.

2. The method of claim 1, wherein the at least one registration instruction comprises an indication of a subsection of a surface of the at least one portion of the patient's body, in which subsection the at least one registration point is to be acquired.

3. The method of claim 2, further comprising:
receiving information indicative of the at least one acquired registration point; and
processing the information indicative of the at least one acquired registration point for obtaining a second transformation between the first coordinate system of the first patient image data and a third coordinate system of a surgical tracking system.

4. The method of claim 3, wherein the information indicative of the at least one acquired registration point has been acquired by the surgical tracking system tracking a registration probe.

5. The method of claim 3, wherein processing the information indicative of the at least one acquired registration point comprises matching a position of the at least one acquired registration point to the first patient image data.

6. The method of claim 3, further comprising:
acquiring the information indicative of the at least one acquired registration point by obtaining at least one position of the registration probe in the third coordinate system; and
determining the second transformation by matching the information indicative of the at least one acquired registration point to the first patient image data.

7. The method of claim 3, further comprising:
obtaining tracking data describing a pose of a surgical instrument in the third coordinate system;
transforming the pose of the surgical instrument into the second coordinate system based on the first transformation and the second transformation;
determining at least one navigation instruction associated with the pose of the surgical instrument in the second coordinate system; and
triggering display of the at least one navigation instruction on the display of the AR device.

8. The method of claim 1, wherein the portion of the patient's body comprises one or more parts of a face of the patient, and wherein the step of determining the first transformation further comprises matching a generic face model to at least one of the first patient image data and the second patient image data.

9. The method of claim 8, wherein the step of determining the first transformation further comprises:
determining a primary deformed face model by matching the generic face model to one of the first patient image data and the second patient image data; and
comparing the primary deformed face model with the other of the first patient image data and the second patient image data to determine the first transformation.

10. The method of claim 9, wherein the generic face model is matched to the one of the first patient image data and the second patient image data such that each of a plurality of predefined landmarks of the generic face model lies on a corresponding landmark of the portion of the patient's body in the one of the first patient image data and the second patient image data.

11. The method of claim 10, wherein the corresponding landmark is a biometric feature of the patient's body.

12. The method of claim 9, wherein the step of comparing the primary deformed face model with the other of the first patient image data and the second patient image data further comprises:
determining a secondary deformed face model by matching the generic face model or the primary deformed face model to the other of the first patient image data and the second patient image data; and
comparing the primary deformed face model with the secondary deformed face model.

13. The method of claim 10, wherein the step of comparing the primary deformed face model with the other of the first patient image data and the second patient image data further comprises:
performing an image analysis on the other of the first patient image data and the second patient image data to determine a position of at least one of the corresponding landmarks in the other of the first patient image data and the second patient image data; and
comparing the determined position of the at least one of the corresponding landmarks in the other of the first patient image data and the second patient image data with a position of one of the plurality of predefined landmarks of the primary deformed face model that lies on the same corresponding landmark in the one of the first patient image data and the second patient image data.

14. The method of claim 12, further comprising:
determining whether a result of the comparing of (i) the primary deformed face model with (ii) the secondary deformed face model or the other of the first patient image data and the second patient image data fulfils one or more predefined acceptance criteria; and
if the result fulfils the one or more predefined acceptance criteria, triggering display of the at least one registration instruction.

15. The method of claim 1, further comprising instructing the surgical tracking system to start tracking after display of the at least one registration instruction has been triggered.

16. The method of claim 1, wherein the second patient image data is indicative of a two-dimensional image acquired by a camera of the AR device or three-dimensional image data acquired by a sensor of the AR device.

17. A system comprising at least one memory and at least one processor, the at least one memory storing instructions which, when executed on the at least one processor, cause the at least one processor to:
obtain first patient image data of at least a portion of a patient's body;
determine at least one registration instruction based on the first patient image data, the at least one registration instruction being indicative of where to acquire at least one registration point relative to a surface of the patient's body;

obtain second patient image data of at least the portion of the patient's body, the second patient image data having been acquired by an augmented reality, AR, device;

determine a first transformation between a first coordinate system of the first patient image data and a second coordinate system of the second patient image data; and based on the at least one registration instruction and the first transformation, trigger display of the at least one registration instruction on a display of the AR device such that a user of the AR device is presented an augmented view with the at least one registration instruction being overlaid onto at least the portion of the patient's body, the augmented view guiding the user where to acquire the at least one registration point.

18. The system of claim 17, further comprising at least one component chosen from the group consisting of the AR device, optionally configured as a head-mounted display, HMD, and a surgical tracking system.

19. The system of claim 18, configured such that the AR device or the patient's body cannot be tracked by the surgical tracking system.

20. A non-transitory computer-readable storage medium storing program code portions which, when executed by at least one processor, cause the at least one processor to perform a method of providing user guidance for obtaining a transformation between a coordinate system of patient image data and a coordinate system of a surgical tracking system, wherein said method comprises:

obtaining first patient image data of at least a portion of a patient's body;

determining at least one registration instruction based on the first patient image data, the at least one registration instruction being indicative of where to acquire at least one registration point relative to a surface of the patient's body;

obtaining second patient image data of at least the portion of the patient's body, the second patient image data having been acquired by an augmented reality, AR, device;

determining a first transformation between a first coordinate system of the first patient image data and a second coordinate system of the second patient image data; and based on the at least one registration instruction and the first transformation, triggering display of the at least one registration instruction on a display of the AR device such that a user of the AR device is presented an augmented view with the at least one registration instruction being overlaid onto at least the portion of the patient's body, the augmented view guiding the user where to acquire the at least one registration point.

* * * * *